(12) United States Patent
Rijkhoff et al.

(10) Patent No.: US 6,836,684 B1
(45) Date of Patent: Dec. 28, 2004

(54) METHOD TO CONTROL AN OVERACTIVE BLADDER

(75) Inventors: Nico J. M. Rijkhoff, Aalborg (DK); Thomas Sinkjaer, Gistrup (DK); Saso Jezernik, Zurich (CH); Warren Grill, Cleveland Heights, OH (US)

(73) Assignee: Neurocon ApS, Aalborg O (DK)

( * ) Notice: Subject to any disclaimer, the term of this patent is extended or adjusted under 35 U.S.C. 154(b) by 0 days.

(21) Appl. No.: 09/830,666

(22) PCT Filed: Oct. 29, 1999

(86) PCT No.: PCT/DK99/00589

§ 371 (c)(1),
(2), (4) Date: Jul. 30, 2001

(87) PCT Pub. No.: WO00/25859

PCT Pub. Date: May 11, 2000

(51) Int. Cl.[7] ............................................... A61N 1/08
(52) U.S. Cl. ........................................................ 607/40
(58) Field of Search .............................. 600/363, 377; 607/40, 41, 115, 116

(56) References Cited

U.S. PATENT DOCUMENTS

| | | | | |
|---|---|---|---|---|
| 3,662,758 A | * | 5/1972 | Glover ........................ 607/40 |
| 3,870,051 A | | 3/1975 | Brindley ...................... 128/422 |
| 4,406,288 A | | 9/1983 | Horwinski et al. ......... 128/422 |
| 4,607,639 A | | 8/1986 | Tanagho et al. ........ 128/419 E |
| 5,188,104 A | * | 2/1993 | Wernicke et al. ............. 607/40 |
| 5,199,430 A | * | 4/1993 | Fang et al. ............. 128/419 E |
| 6,354,991 B1 | * | 3/2002 | Gross et al. ................... 600/29 |
| 6,505,074 B2 | * | 1/2003 | Boveja et al. ................ 607/41 |
| 6,587,725 B1 | * | 7/2003 | Durand et al. ................ 607/42 |

FOREIGN PATENT DOCUMENTS

WO    95/16491    6/1995

OTHER PUBLICATIONS

Sengupta et al.; Mechanosensitive Properties of Pelvic Nerve Afferent Fibers Innervating the Urinary Bladder of the Rat; Journal of Neurophysiology, vol. 72, No. 5, 1994, 2420–2430.

Vodušek et al.; Detrusor Inhibition on Selective Pudendal Nerve Stimulation in the Perineum; Neurourology and Urodynamics; 6: 389–393, 1988.

Wiart et al.; The effects of capsaicin on the neurogenic hyperreflexic detrusor. A double blind placebo controlled study in patients with spinal cord disease. Preliminary results; Spinal Cord (1998), 36: 95–99.

Binard et al.; Intermittent Catheterization the Right Way! (Volume vs. Time–Directed) ; The Journal of Spinal Cord Medicine; vol. 19, No. 3, 194–196.

Rijkhoff et al.; Acute Animal Studies on the Use of an Anodal Block to Reduce Urethral Resistance in Sacral Root Stimulation; IEEE Transactions on Rehabilitation Engineering, vol. 2, No. 2, 1994; 92–99.

(List continued on next page.)

*Primary Examiner*—Jeffrey R. Jastrzab
*Assistant Examiner*—Frances P. Oropeza
(74) *Attorney, Agent, or Firm*—Jacobson Holman PLLC

(57) ABSTRACT

A method to control an overactive bladder and to estimate bladder volume using an implanted sensor having at least one nerve electrode to sense electrical signals. The method includes detecting events from nerve signals, generating electrical pulses for stimulating nerves, and stimulating the nerves to inhibit detrusor contraction. Bladder volume may also be estimated based on the amplitude of the detected nerve signals and/or the time between two detected nerve signals from consecutive detrusor contractions.

13 Claims, 2 Drawing Sheets

OTHER PUBLICATIONS

Rijkhoff et al.; Selective detrusor activation by sacral ventral nerve–root stimulation: results of intraoperative testing in humans during implantation of a Finetech–Brindley system; World J Urol (1998) 16: 337–341.

Koldewijn et al.; Bladder Pressure Sensors in an Animal Model; Journal of Urology, 151, 1379–1384, 1994.

Wheeler, Jr. et al.; Bladder Inhibition by Penile Nerve Stimulation in Spinal Cord Injury Patients; The Journal of Urology, vol. 147, 100–103, 1992.

Van Kerrebroeck et al.; Intradural sacral rhizotomies and implantation of an anterior sacral root stimulator in the treatment of neurogenic bladder dysfunction after spinal cord injury. Surgical technique and complications; World Journal of Urology, 9:126–132, 1991.

Koldewijn et al.; Bladder Compliance After Posterior Sacral Root Rhizotomies and Anterior Sacral Root Stimulation; Journal of Urology, 151, 955–960, 1994.

Sidi et al.; Augmentation Enterocystoplasty for the Management of Voiding Dysfunction in Spinal Cord Injury Patients; The Journal of Urology, vol. 143, pp. 83–85, 1990.

Lefurge et al,; Chronically Implanted Intrafascicular Recording Electrodes; Annals of Biomedical Engineering; vol. 19, 1991, pp. 197–207.

* cited by examiner

METHOD TO CONTROL AN OVERACTIVE BLADDER

BACKGROUND OF THE INVENTION

1. Field of the Invention

This application concerns a method to control an overactive bladder and to estimate bladder volume, comprising an implanted sensor, which sensor comprises at least one nerve electrode to sense electrical signals, means for stimulation of nerves to inhibit detrusor contraction, an electronic unit to detect events from nerve signals and generate electrical pulses for stimulating nerves.

2. Description of the Related Art

U.S. Pat. No. 4,406,228 discloses a system that purportedly conditions pelvic floor musculature by means of neurostimulation for the purpose of controlling urinary loss. Such system includes stimulation apparatus for applying electrical pulses to electrodes implanted in the abdominal region or to a plug positioned in an anus. The plug contacts the spincter muscle of the anus for the alleged purpose of inhibiting bladder contraction in response to excitation of the plug.

In this way the bladder volume is not measured, which can lead to bladder over distensions, and can lead to bladder rupture.

The storage phase of the micturition cycle requires a stable bladder with high compliance (i.e. a relaxed bladder) and closed urethral outlet. However, due to the feedback system the bladder may easily become unstable. Any stimulus that elicits a small burst of impulses in the mechanoreceptor afferents, such as coughing and jumping, may trigger an involuntary micturition reflex and cause urine leakage. To prevent this from happening, the neural control system is equipped with several inhibitory circuits, both at spinal and supraspinal levels, which prevent the detrusor muscle from contracting. However, these inhibitory circuits are susceptible to a variety of neurologic disorders. Therefore, patients with neurologic disorders frequently suffer from urinary incontinence due to involuntary detrusor contractions.

The impaired storage function could in principle be improved by methods that decrease the sensitivity of the bladder afferents, decrease the activity of the bladder efferents or increase the bladder volume/capacity. Available treatment options are therefore: surgical augmentation of the bladder [Sidi et al., 1990], surgical deafferentation of the bladder [Koldewijn et al., 1994], the use of anticholinergic drugs and the use of intravesical capsaicin [Wiart et al., 1998].

Bladder inhibition by electrical stimulation has been described before [e.g. Vodušek et al., 1988; Wheeler et al., 1992] but only continuous stimulation was used, i.e. stimulation is permanent except during voiding.

SUMMARY OF THE INVENTION

The objects of the invention are:
1) treatment of involuntary loss of urine (incontinence) due to involuntary detrusor contractions (detrusor overactivity)
2) estimation of bladder volume. This finds particular application in patients who use aids to empty their bladder e.g. intermittent catherisation or electrical stimulation.

The invention finds particular application in patients where the involuntary detrusor contraction is associated with a neurologic disorder.

Treatment of detrusor overactivity and estimation of bladder volume can be achieved by a method as described in the first paragraph using a closed loop stimulation system to allow event-driven inhibition of the bladder where stimulation is only applied when an undesired bladder contraction occurs, and an implanted sensor comprising at least one nerve electrode to sense electrical signals from nerves innervating the bladder. Sensing electrical signals related to mechanical bladder activity via said sensor, the method detects the onset of a bladder contraction and estimates bladder volume using signal processing methods, activating an inhibitory neural circuit by stimulating afferent nerve fibers.

By this method no nerves have to be cut, and no irreversible surgery has to be done. Stimulation of neural tissue only takes place when needed, and the volume of the bladder is monitored. The present invention uses electrical stimulation to inhibit the bladder. Inhibition of the bladder by electrical stimulation is possible since, besides the mentioned neural inhibitory circuits, additional spinal inhibitory circuits exist to prevent involuntary leakage during, e.g., defecation, coitus and physical activity. Activation of the afferent paths of these neural circuits has two effects: they activate the inhibitory sympathetic neurons to the bladder and they provide central inhibition of the preganglionic detrusor-motoneurons through a direct route in the spinal cord. These additional inhibitory reflexes are not suppressed during micturition, which means that they are quite capable of interrupting a detrusor contraction. Activation of these reflexes by electrical stimulation is a nondestructive alternative method for patients who are refractory to drugs, cannot tolerate the side effects or for other reasons do not accept a drug treatment.

Primarily, the recorded nerve signals come from afferents innervating mechanoreceptors located in the bladder wall. By detecting the onset of the bladder contraction, the stimulator can be activated only when contraction occurs, and continuous stimulation is not necessary. This minimises the risk of neural damage due to the stimulation. In addition, if the patient can sense the stimulation, the duration of stimulation should be minimised to minimise the discomfort.

The step of implanting a sensor might comprise the step of implanting a nerve cuff electrode. The intrafasicular electrode is flexible and small, and may be preferred in locations where limited space is available.

The step of implanting a sensor might comprise the step of implanting an intrafasicular electrode [Lefurge et al., 1991]. The intrafasicular electrode is flexible and smaller, and might be preferred in locations where limited space is available.

The electrodes can be used to detect efferent or afferent nerve activity. The same electrode could be used to record both types of nerve signals.

The electrode can be placed on a nerve that contains afferent nerve fibres innervating mechanoreceptors located in the bladder. In this way information about the status of the bladder can be obtained.

The electrode can be located at the intradural or extradural dorsal sacral nerve roots. In this way the electrodes can be placed at a mechanically stable position, and the nerve roots are relatively long, which enables easy placement of electrodes.

The electrode can be placed on a nerve that contains efferent nerve fibres innervating the bladder, so bladder activation can be monitored.

The electrode can be located at the intradural or extradural ventral sacral nerve roots. In this way the electrodes can be placed at a mechanically stable position, and the nerve roots are relatively long, which enables easy placement of electrodes.

The electrode might be located at at least one of the preganglionic pelvic nerve branches and postganglionic nerve branches. In this way nerve signals from the bladder can be recorded more selectively without contamination with signals from other organs.

Preferably two different nerve signals can be used to detect a detrusor contraction, where the first signal comes from afferent nerves innervating the bladder, and the second signal comes from efferent nerves innervating the detrusor muscle. In this way the detrusor contraction can be detected more reliably.

Activating a neural circuit that inhibits the bladder contraction can be done by stimulating afferent nerve fibres, innervating mechanoreceptors, located in the glans of the penis or clitoris. In this way an ongoing detrusor contraction can be aborted or stopped and leakage of urine will be prevented.

The bladder volume can be derived from the amplitude of the recorded afferent signal. By measuring of the bladder volume the patient can be informed about his/her bladder volume.

The bladder volume can be derived from the time between two consecutive detrusor contractions. By measuring of the bladder volume, the patient can be informed about his/her bladder volume.

The bladder volume can be derived from both the amplitude of the recorded nerve signal and the time between two consecutive detrusor contractions. This way the bladder volume can be estimated in a more reliable way.

In the following the invention will be detailed described partly with reference to drawings.

DETAILED DESCRIPTION OF THE PREFERRED EMBODIMENTS

Figure 1:
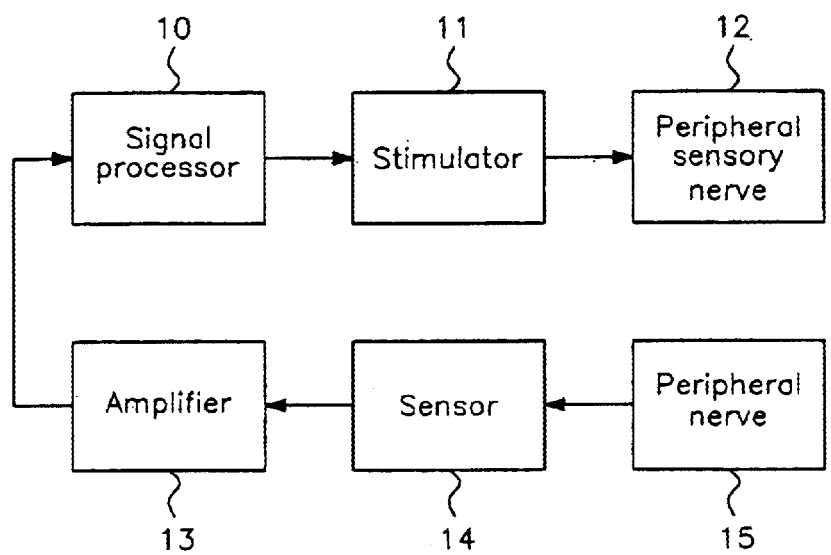
FIG. 1 shows a block diagram of event driven stimulation system to treat an overactive bladder.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Mechanoreceptors located in the bladder wall act as tension receptors and respond in graded fashion to increases in bladder volume and intravesical pressure. It has been shown that a close relationship between afferent nerve activity and the pattern of intravesical pressure changes is best observed when the activity of many afferent nerve fibres is summed. Sensor 14 comprises an implantable nerve cuff electrode. This type of electrode surrounds the selected nerve in close proximity so currents generated by the nerve fibres result in sufficiently large voltage differences in the volume within the cuff so that they can be detected by the electrode. However, other electrode configurations such as intrafasicular electrodes could also be used to detect the efferent nerve activity. The electrode needs to be placed on a peripheral nerve 15 that contains afferent nerve fibres innervating mechanoreceptors located in the bladder. Possible locations for the electrode are therefore: intradural dorsal sacral nerve roots (S2–S4), extradural sacral nerve roots (S2–S4), preganglionic pelvic nerve branches and postganglionic nerve branches. An alternative method to detect a bladder contraction is to record from the efferent nerve fibres that innervate the detrusor muscle. An increase in the efferent signal results in a detrusor contraction so an increased efferent signal indicates a detrusor contraction. Possible locations for the electrode to record efferent signals from peripheral nerve 15 are: intradural ventral sacral nerve roots (S2–S4), extradural sacral nerve roots (S2–S4), preganglionic pelvic nerve branches and postganglionic nerve branches.

The output of the sensor 14 is passed through a circuit 13 that includes an amplifier and a filter. The output of circuit 13 is passed to circuit 10, which contains a detection algorithm that allows the detection of the onset of a sudden rise in intravesical pressure or a detrusor contraction. The detection algorithm takes place in a signal processor 10, which will pass a trigger signal to stimulator 11 when it detects such a pressure rise. The stimulator 11 includes one or more electrodes placed on peripheral sensory nerves 12. The stimulator 11 produces, in response to the trigger signal from circuit 10, an electrical potential difference, which will result in an electrical current through the electrode and adjacent nervous tissue. A rapid change in this electrical current activates or stimulates nerve fibres causing the production of action potentials in peripheral nerve 12. It has been shown that activation of afferent nerve fibres, innervating mechanoreceptors located in the glans of the penis or clitoris, has a strong inhibitory effect on the bladder. To obtain the desired effect of bladder inhibition upon stimulation the afferents should be stimulated somewhere along their course from mechanoreceptors to the sacral spinal cord. This means that possible locations for the electrode to be placed on peripheral nerve 12 are: dorsal penile/clitoris nerve, pudendal nerve, extradural sacral nerve roots (S2–S4) and intradural dorsal sacral nerve roots (S2–S4).

Figure 2:
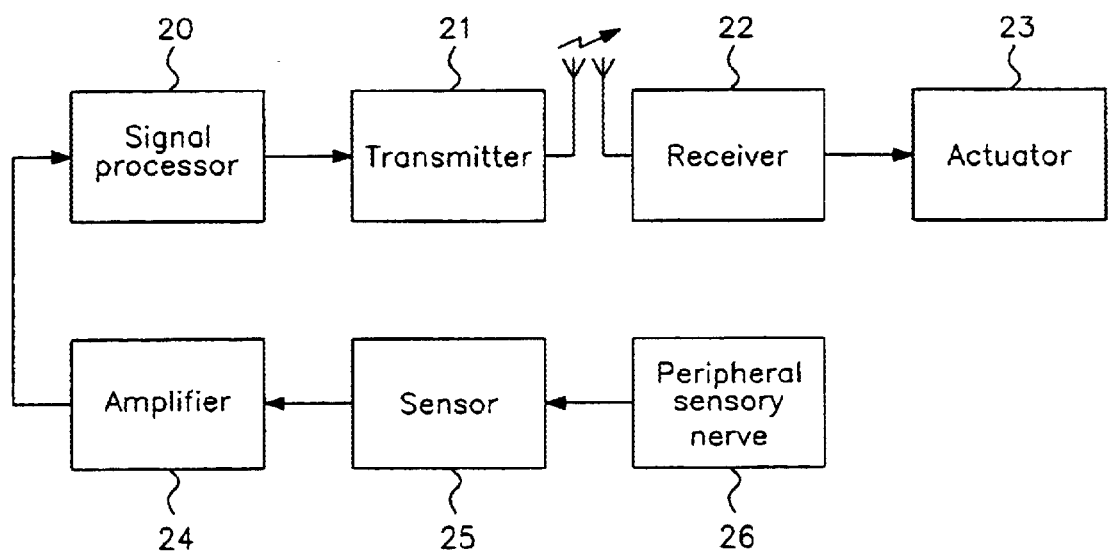
FIG. 2 shows a block diagram of a bladder volume monitoring system.

A system for monitoring the bladder volume is shown in FIG. 2. Mechanoreceptors located in the bladder wall act as tension receptors and respond in graded fashion to increases in bladder volume and intravesical pressure. It has been shown that a close relationship exist between afferent nerve activity and bladder volume. In addition, bladder volume could be estimated from the time between two consecutive hyperreflexic bladder contractions since the number of contractions per time unit is proportional to the bladder volume. The preferred nerve electrode 25 for this purpose is an implantable nerve cuff electrode, although other electrode configurations could also be used. The sensor 25 comprises an electrode, which needs to be placed on a peripheral sensory nerve 26 that contains afferent nerve fibres innervating mechanoreceptors located in the bladder. Possible locations for the sensor 25 are therefore: intradural dorsal sacral nerve roots (S2–S4), extradural sacral nerve roots (S2–S4), preganglionic pelvic nerve branches and postganglionic nerve branches. Sensor 25 could be the same one as sensor 14 so the systems of FIG. 1 and FIG. 2 share the same electrode.

The output of the sensor 25 is passed through a circuit 24 that includes an amplifier and a filter. The output of circuit 24 is passed to signal processing unit 20, which contains an estimation algorithm that allows estimation of bladder volume. If the estimated volume exceeds the volume threshold then a trigger signal will be passed to transmitter 21. Upon receiving a trigger, transmitter 21 sends a signal to receiver 22 using radio waves. Receiver 22 is placed outside the body and will, upon receiving a signal from transmitter 21, pass a signal to actuator 23. Actuator 23 will alert the user that the bladder volume exceeded the volume threshold. Various devices could be used as actuator such as a buzzer, a vibrator, etc.

Figure 3:
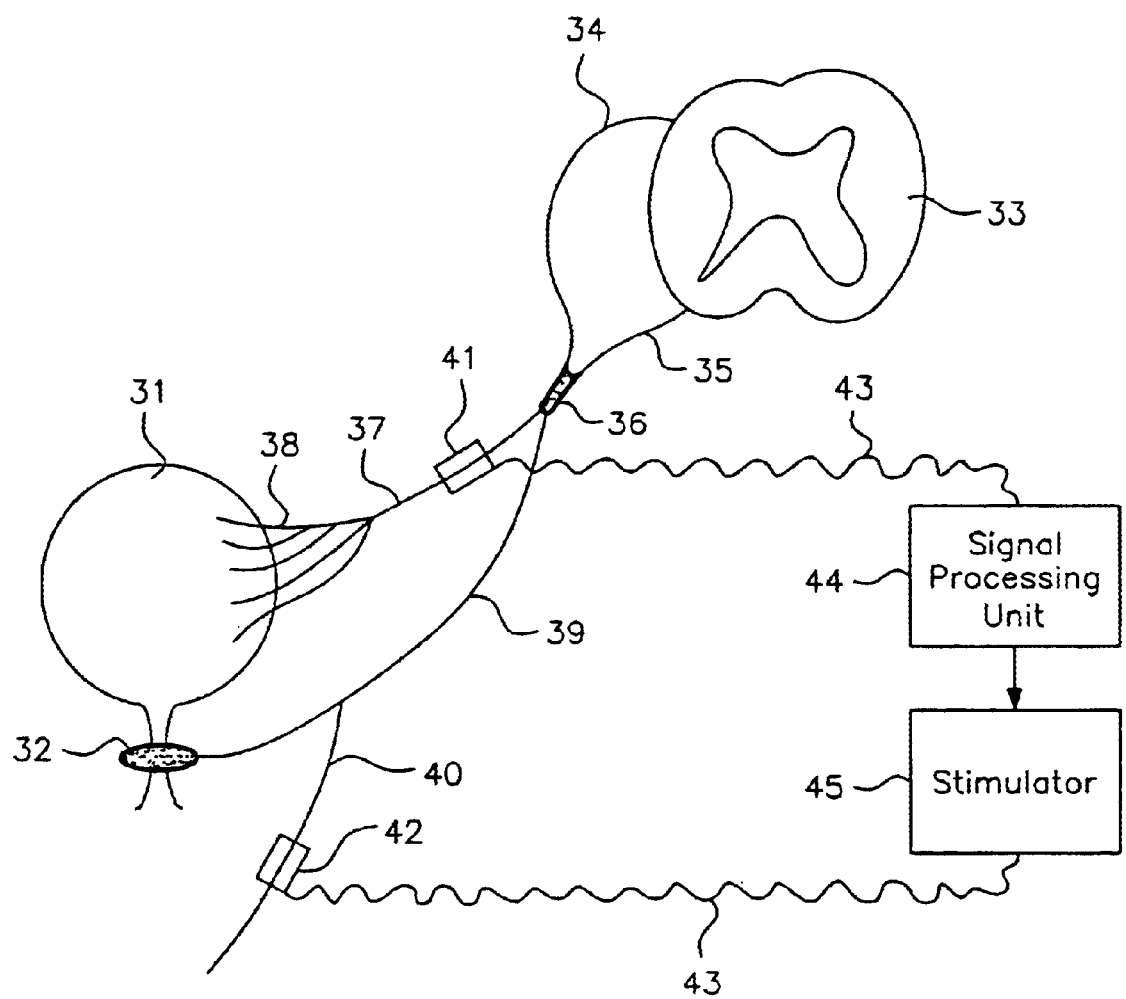
FIG. 3 shows schematically how the invention is applied.

FIG. 3 shows in detail the elements of the invention. A bladder 31 with a closing mechanism comprising a sphincter 32 together with the innervating peripheral nerves, which comprises intradural dorsal sacral root 34, intradural ventral sacral root 35, extradural sacral root 36, preganglionic pelvic nerve 37, postganglionic pelvic nerve 38 and pudendal nerve 39. In addition, the dorsal penile/clitoral nerve 40 is shown. These nerves relay information to and from the spinal cord 33. A recording electrode 41 senses information from the nerves 37, and electrical information is transmitted through an electrode lead 43 to a signal processing unit 44, which is connected to a stimulator 45. The signal from the stimulator 45 is transmitted through an electrode lead 43 to a stimulation electrode 42, which stimulates nerve 40.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for controlling an overactive bladder, comprising the steps:

detecting nerve signals from nerves innervating the bladder;

detecting a bladder event from the nerve signals;

generating electrical pulses in response to the detected event;

stimulating afferent nerves using the generated electrical pulses in order to inhibit detrusor contraction of the bladder.

2. A method as defined in claim 1, wherein the detected nerve signals primarily come from afferent nerve fibres innervating mechanoreceptors in the bladder wall.

3. A method as defined in claim 1, wherein the detected nerve signals come from efferent nerve fibres innervating the bladder.

4. A method as defined in claim 1, wherein two different signals are used to detect detrusor contractions, a first signal coming from afferent nerves innervating the bladder, and a second signal coming from efferent nerves innervating the detrusor muscle.

5. A method as defined in claim 1, wherein neural circuits inhibiting bladder contraction are stimulated by activating an inhibitory spinal reflex by stimulating afferent nerve fibres innervating mechanoreceptors located in the glans of the penis or clitoris.

6. A method as defined in claim 5, wherein a stimulation electrode is located at a nerve belonging to the group consisting of a dorsal penile/clitoris nerve, a pudendal nerve, an extradural sacral nerve root and an intradural dorsal sacral nerve root.

7. A method as defined in claim 1, wherein both a detecting electrode and a stimulation electrode are located at either the intradural dorsal sacral nerve roots or the extradural sacral nerve root.

8. A method as defined in claim 7, wherein the dorsal sacral nerve roots belong to the group S2–S4.

9. The method as set forth in claim 1, further comprising the step of estimating bladder volume in response to the detected signals using signal-processing methods.

10. The method as set forth in claim 9, wherein said step of estimating is performed using an amplitude of the detected nerve signals.

11. The method as set forth in claim 9, wherein said step of estimating is performed using a time between two detected nerve signals derived from two consecutive detrusor contractions.

12. The method as set forth in claim 9, wherein said step of estimating is performed using an amplitude of the detected nerve signals and a time between two detected nerve signals derived from two consecutive detrusor contractions.

13. The method as set forth in claim 9, further comprising the steps of:

transmitting, from a transmitter placed inside a user's body, a signal when a predetermined threshold value for bladder volume has been exceeded;

receiving the signal with a receiver located outside the user's body;

actuating an alert in response to the received signal for alerting the user that the threshold value has been reached.

* * * * *

UNITED STATES PATENT AND TRADEMARK OFFICE
CERTIFICATE OF CORRECTION

PATENT NO.    : 6,836,684 B1  
DATED         : December 28, 2004  
INVENTOR(S)   : Rijkhoff et al.

It is certified that error appears in the above-identified patent and that said Letters Patent is hereby corrected as shown below:

<u>Title page,</u>  
Insert -- [30]    Foreign Application Priority Data  
        Oct. 30, 1998 (DK).........................1998  01396 --

Signed and Sealed this

Seventh Day of June, 2005

JON W. DUDAS  
*Director of the United States Patent and Trademark Office*